United States Patent [19]

Bruynes et al.

[11] 4,067,986
[45] Jan. 10, 1978

[54] NOVEL PENICILLANIC ACID

[75] Inventors: Cornelis Adrianus Bruynes, Koudekerk an den Rijn; Johannes Karel Van der Drift, Delft, both of Netherlands

[73] Assignee: Gist-Brocades N.V., Delft, Netherlands

[21] Appl. No.: 624,276

[22] Filed: Oct. 20, 1975

[30] Foreign Application Priority Data

Oct. 21, 1974 United Kingdom ............... 45480/74

[51] Int. Cl.² ..................... A61K 31/43; C07D 499/68
[52] U.S. Cl. .................................. 424/271; 260/239.1
[58] Field of Search ...................... 260/239.1; 424/271

[56] References Cited

U.S. PATENT DOCUMENTS

| | | | |
|---|---|---|---|
| 3,558,601 | 1/1971 | Ekström et al. | 260/239.1 |
| 3,674,776 | 7/1972 | Long et al. | 260/239.1 |
| 3,923,787 | 12/1975 | Clayton et al. | 260/239.1 |
| 3,935,189 | 1/1976 | Fenes et al. | 260/239.1 |
| 3,939,149 | 2/1976 | König et al. | 260/239.1 |
| 3,945,994 | 3/1976 | Bruynes et al. | 260/239.1 |

FOREIGN PATENT DOCUMENTS 2,405,894  9/1974  Germany ..................... 260/239.1

*Primary Examiner*—Gerald A. Schwartz
*Attorney, Agent, or Firm*—Hammond & Littell

[57] ABSTRACT

Penicillanic acid derivatives of the formula

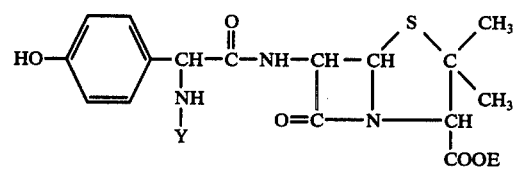

wherein E is selected from the group consisting of hydrogen, a salt forming cation, and an ester forming residue which is known to improve the absorption characteristics of penicillanic compounds after oral administration to humans or animals, and Y is a group of the formula

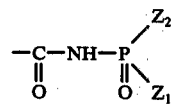

wherein $Z_1$ and $Z_2$ are individually selected from the group consisting of lower alkoxy, optionally substituted phenoxy, optionally substituted benzyl and benzyloxy group, optionally substituted lower alkyl, optionally substituted phenyl, hydroxy and -OM wherein M represents a salt forming cation, and hydrates of the said salts having antibacterial properties and their preparation and novel intermediates.

11 Claims, No Drawings

NOVEL PENICILLANIC ACID

STATE OF THE ART

Some semi-synthetic penicillins have been developed and marketed on a large scale during the last two decades, e.g. ampicillin, amoxycillin, sulbenicillin, carbenicillin, dicloxacillin and nafcillin. Although these semi-synthetic penicillins have appeared to be effective in combatting a large number of infectious diseases caused by several microorganisms, the need for some additional antibiotics acting effectively against some specific microorganisms, such as Pseudomonas and Proteus species, still remains.

OBJECTS OF THE INVENTION

An object of the invention is to provide new derivatives of amoxycillin, viz. 6-[α-amino-(p-hydroxy-benzylcarbonamido]penicillanic acid, having interesting activities against microorganisms of, for example, the Pseudomonas and/or Proteus species in addition to the already known good activities of amoxycillin.

It is another object of the invention to provide a process for the preparation of the compounds of formula I and to provide novel intermediates therefore.

It is a further object of the invention to provide novel antibacterial compositions.

It is an additional object of the invention to provide a novel method of combatting bacteria, particularly bacterial infections in warm-blooded animals.

These and other objects and advantages of the invention will become obvious from the following detailed description.

THE INVENTION

The novel penicillanic acid compounds of the invention have the formula

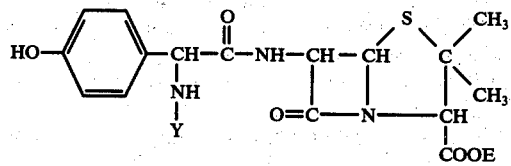

wherein E is selected from the group consisting of hydrogen, a salt forming cation, and an ester forming residue which is known to improve the absorption characteristics of penicillanic compounds after oral administration to humans or animals, and Y is a group of the formula

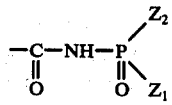

wherein $Z_1$ and $Z_2$ are individually selected from the group consisting of lower alkoxy, optionally substituted phenoxy, optionally substituted benzyl and benzyloxy group, optionally substituted lower alkyl, optionally substituted phenyl, hydroxy and —OM wherein M represents a salt forming cation, and hydrates of the said salts.

The substituents which may optionally be present on a phenyl nucleus of groups within the definition of symbol Y are selected from halogen, nitro, cyano, lower alkyl and lower alkoxy. The term "lower" as applied herein to alkoxy and alkyl groups means that the group in question contains at most 6 carbon atoms.

Ester groups within the definition of symbol E, which may improve the physical absorption characteristics of the compounds of formula I, may be selected from, for example, groups of the formula

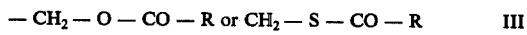

wherein R represents a straight- or branched-chain alkyl of 1 to 4 carbon atoms optionally substituted by at least one substituent selected from lower alkoxy, lower alkylthio and halo(lower)alkyl.

The salt forming cations within the definitions of symbols E and M are those which form non-toxic, pharmaceutically acceptable salts of the compounds of formula I such as alkali metal salts like sodium and potassium or alkaline earth metal salts like calcium salts, ammonium salts of amine salts, e.g. tri(lower)alkylamine, procaine or benzylamine salts. Hydrates of salts of the compounds of formula I are within the scope of the invention.

Examples of groups within the scope of formula II are di(lower)alkoxyphosphinylaminocarbonyl, diphenoxyphosphinylaminocarbonyl, diphenylphosphinylaminocarbonyl, di(lower) alkylphosphinylaminocarbonyl, hydroxy-benzylphosphinylaminocarbonyl, hydroxy-(lower)alkoxyphosphinylaminocarbonyl, hydroxy-phenylphosphinylaminocarbonyl, hydroxy-(lower)alkylphosphinylaminocarbonyl, (lower)-alkoxybenzyloxyphosphinyl-aminocarbonyl, phenyl-benzyloxyphosphinylaminocarbonyl, lower alkylbenzyloxyphosphinylaminocarbonyl, dibenzyloxyphosphinylaminocarbonyl, dihydroxyphosphinylaminocarbonyl, (lower) alkoxybenzylphosphinylaminocarbonyl and (lower) alkoxyphenylphosphinylaminocarbonyl.

Typical compounds of the invention are D-6-{α-[3-(benzyloxy(ethyl)phosphinyl)ureido]-p-hydroxybenzylcarbonamido}penicillanic acid, D-6-{α-[3-(benzyloxy(ethoxy)phosphinyl)ureido]-p-hydroxybenzylcarbonamido}-penicillanic acid, D-6-{α-[3-(dibenzyloxyphosphinyl)ureido]-p-hydroxybenzylcarbonamido}•penicillanic acid, D-6-{α-[3-(hydroxy(ethyl)phosphinyl)ureido]-p-hydroxybenzylcarbonamido}penicillanic acid, D-6-{α-[3-(hydroxy(ethoxy)phosphinyl)ureido]-p-hydroxybenzylcarbonamido}penicillanic acid, D-6-{α-[3-(hydroxy(benzyloxy)phosphinyl)ureido]-p-hydroxybenzylcarbonamido}penicillanic acid, D-6-{α-[3-(benzyloxy-(methoxy)phosphinyl)ureido]-p-hydroxybenzylcarbonamido}-penicillanic acid, D-6-{α-[3-(hydroxy (methoxy)phosphinyl)-ureido]-p-hydroxybenzylcarbonamido}penicillanic acid, D-6-{α-[3-(dihydroxyphosphinyl)ureido]-p-hydroxybenzylcarbonamido}penicillanic acid, D-6-{α-[3-(benzyloxy(methyl)phosphinyl)-ureido]-p-hydroxybenzylcarbonamido}penicillanic acid, D-6-{α-[3-(benzyloxy(i-propyl)phosphinyl)ureido]-p-hydroxybenzylcarbonamido}penicillanic acid, D-6-{α-[3-(benzyloxy (t-butyl)phosphinyl)-ureido]-p-hydroxybenzylcarbonamido}penicillanic acid, D-6-{α-[3-(benzyloxy (t-butoxy)phosphinyl)-ureido]-p-hydroxybenzylcarbonamido}penicillanic acid, D-6-{α-[3-(hydroxy(methyl)phosphinyl) ureido]-p-hydroxybenzylcarbonamido}penicillanic acid, D-6-{α-[3-(hydroxy (i-propyl)phosphinyl) ureido]-p-hydroxybenzylcarbonamido}penicillanic acid, D-6-{α-[3-(hydroxy(t- butoxy)phosphinyl)ureido]-p-hydroxybenzylcarbonamido}penicillanic acid, D-6-{α[3-(hydroxy (t-butyl) phosphinyl) ureido]-p-hydroxybenzylcarbonamido}penicillanic acid, D-6-{α[3-(hydroxy (i-propoxy) phosphinyl)ureido[-p-hydroxybenzylcarbonamido}penicillanic acid, and their sodium, potassium or ammonium or amine salts (mono, di- and tri-valent salts), and pharmaceutically acceptable esters having ester groups of formula III, with the compounds of formula I wherein $Z_1$ and/or $Z_2$ is hydroxy or $\sim$ OM, being preferred representatives. Especially the compounds, wherein $Z_1$ is hydroxy or OM, and $Z_2$ is methoxy or ethoxy, have showed interesting antimicrobial activities. As usual, the D modification of these compounds shows the most interesting activity.

The compounds of formula I may be prepared by known methods for the preparation of structurally similar penicillins. Thus, according to another feature of the invention, the compounds of formula I are prepared by reacting a compound of the formula

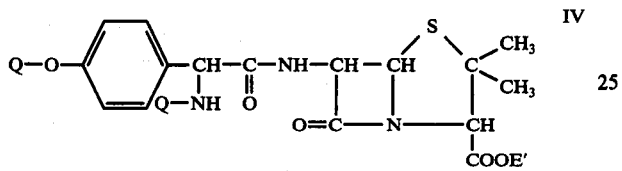
IV wherein Q is hydrogen or silicon or phosphorous carrying substituents selected from the group consisting of lower alkyl, halo lower alkyl, aryl, aralkyl, lower alkoxy, haloalkoxy, lower alkylthio, aralkoxy, di(lower)alkylamino, lower alkoxyalkyl, and alkylenedioxy and halogen (preferably tri (lower) alkylsilyl, e.g. trimethylsilyl) and E' is a group protecting the carboxy radical, preferably a group which can, if desired, be easily removed after the reaction, e.g. by hydrolysis, hydrogenation or a substitution reaction using a basic or nucleophilic reagent, and which does not interfere with the reaction, with a compound of the formula

V wherein $Z_1'$ and $Z_2'$ have the above definition or represent groups which may be easily converted into a group within the definition of $Z_1$ and $Z_2$, in an organic solvent at temperatures of from $-30°$ C to $+30°$ C, preferably between $-5°$ and $+5°$ C and preferably under anhydrous conditions, optionally followed by removal of the protecting group E' and the group(s) Q, when a silicon or phosphorus containing group, from the compound so obtained.

The starting materials of formula IV may be prepared by known methods. For example, the compound wherein the symbols Q are hydrogen and E' is hydrogen, i.e. amoxycillin, can be prepared by the methods described in British Pat. Nos. 873,049; 959,853; 978,178; 1,339,605 and 1,347,979; Belgian Pat. Nos. 676,594; 790,466; 737,848 and 751,106; Dutch Specification No. 7,215,359; South African Specification Nos. 64/695, 66/1304, 67/5627 and 72/05231; or German OLS No. 2240422. Silyl derivatives and esters of amoxycillin of formula IV can be prepared therefrom by known procedures.

An alternative method for the preparation of compounds of formula I comprises reacting acetic acid derivatives of the formula

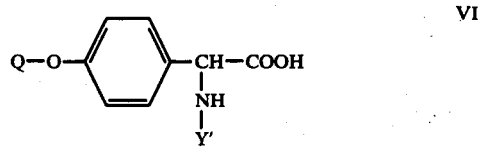
VI wherein Q is as defined hereinbefore and wherein Y' is Y or a group which may be easily converted into a group within the definition of Y (which may be attacked or be influenced under the reaction conditions) after the reaction, with 6-aminopenicillanic acid or a derivative thereof, in the presence of a carbodiimide [e.g. dicyclohexylcarbodiimide, 1-ethyl-3-(3-dimethylamino-propyl) carbodiimide optionally mixed with 1-hydroxy-benzotriazole and 1-cyclohexyl-3-{2-(N-methylmorpholino)ethyl}carbodiimide] as condensing agent.

Derivatives of 6-aminopenicillanic acid, which also may be used, are those of the formula

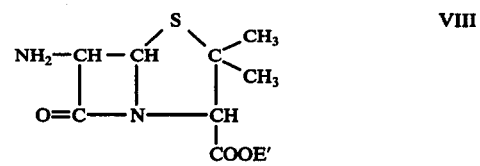
VIII wherein E' is a salt forming residue, a protecting group which can be easily removed after the reaction and does not interfere with it or a pharmaceutically acceptable absorption improving, ester residue. Examples of easily removable protecting residues of E' in the foregoing formulae are an optionally substituted benzyl (e.g. p-nitrobenzyl, p-methoxybenzyl), benzhydryl, phenacyl (e.g. p-halo-substituted phenacyl), 2,2,2-trichloroethyl, trityl, t-butyl, isobornyl, or a silicon or phosphorous atom carrying substitutents selected from the group consisting of lower alkyl, halolower alkyl, aryl, aralkyl, lower alkoxy, haloalkoxy, lower alkylthio, aralkoxy, di(lower)alkylamino, lower alkoxyalkyl and alkylenedioxy and halogen.

The required starting material, D(-)2-amino-2-(p-hydroxyphenyl) acetic acid, for the preparation of the starting acids of formula VI or activated derivatives thereof, are known from, for example, German Offenlegenschrift No. 2355785 and Dutch Patent Specification No. 7311012.

The acids of the formula VI are novel compounds and as such constitute a feature of the invention. They may be prepared by reacting a compound of the formula

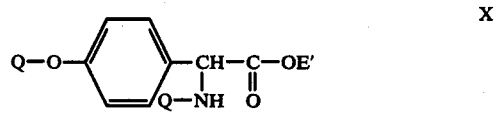
X wherein Q and E' are as hereinbefore defined, with a compound of formula V in an inert organic solvent at temperatures of from $-30°$ C to $+30°$ C, preferably between $-5°$ C and $+5°$ C, and preferably under anhydrous conditions, followed by removal of the protecting group E' and any other protecting group, if desired. Preferably, the obtained acid of formula VI may be converted directly in situ into a compound of formula I by adding to the obtained reaction solution a suitable reactant as hereinbefore indicated.

The starting compounds of formula V may be prepared by methods known per se, as described in for example: G. I. Derkatsch, Angew. Chem. Vol. 81, No. 11, 407–436 (1969), L. I. Samari et al., Zh. Obshch. Khim, 39, 1511 (1969), G. I. Derkach et al, Obshch. Khim. Vol. 38, No. 8, p. 1784 to 1788 (1968), E. S. Gubnitskaya et al., Zh. Obshch. Khim, 40, 1205 to 1210 (1970), L. I. Samarai et al., Zh. Obshch. Khim Vol. 39, No. 8, 1712 to 1715 (1969), A. V. Narbut et al., Zh. Obshch. Khim. Vol. 38, No. 6, p. 1321 to 1324 (1968) and G. Tomaschewski et al., Arch. Pharm. 301, p. 520 (1968).

The compounds of formula I are preferably employed for therapeutic purposes in the form of a non-toxic pharmaceutically acceptable salt such as the sodium, potassium, ammonium or calcium salt. Other salts that may be used include the non-toxic, suitably crystallizing salts with organic bases such as amines, for example, trialkylamines, procaine and dibenzylamine.

In the treatment of bacterial infections, the antibacterial compounds of this invention can be administered topically, orally and parenterally in accordance with conventional procedures for antibiotic administration. They are administered in dosage units containing an effective amount of the active ingredient in combination with suitable physiologically acceptable carriers or excipients. The dosage units can be in the form of liquid preparations, such as solutions, suspensions, dispersions or emulsions or in a solid form such as powders, tablets and capsules.

Accordingly, the invention includes pharmaceutical compositions comprising an effective amount of at least one compound of formula I in association with a suitable physiologically acceptable carrier or excipient. Such pharmaceutical compositions can also include one or more therapeutic ingredients in addition to a compound of the invention. The term "effective amount" as used herein in relation to the described compounds means an amount which is sufficient to destroy or inhibit the growth of susceptible microorganisms when administered in the usual manner, in other words an amount which is sufficient to control the growth of bacteria. The magnitude of an effective amount can be easily determined by those skilled in the art through standard procedures for determining the relative activity of antibacterial agents when utilized against susceptible organisms via the various available routes of administration.

Suitable carriers and excipients may be any convenient, physiologically acceptable ingredient which can serve to facilitate administration of the therapeutically active compound. Carriers may provide some ancillary function such as that of a diluent, flavor masking agent, binding agent, action delaying agent or stabilizer. Examples of carriers include water, which can contain gelatin, acacia, alginate, dextran, polyvinylpyrrolidone or sodium carboxymethyl cellulose, aqueous ethanol, syrup, isotonic saline, isotonic glucose, starch, lactose, or any other such material commonly used in the pharmaceutical and veterinary industry.

Another aspect of the invention includes a method for inhibiting the growth of bacteria by applying to the habitat of the bacteria an effective amount of the antibacterial compounds described herein. For example, the method can be applied to the treatment of bacterial infections in animals by administering to the host an effective amount of an antibacterial compound of the invention, usually 10 to 200 mg/kg depending upon the method of administration and the specific compound.

The novel penicillanic acid derivatives according to the formula I may also be used as growth promotors for ruminant animals. They are also useful in in vitro applications, such as in liquids for disinfecting purposes at a concentration of 0.1 to 1% by weight dissolved or suspended in a suitable inert carrier for application by washing or spraying.

Some typical members belonging to the class of compounds according to the invention were tested for antibiotic activity in vitro by means of an agar serial dilution test carried out as follows: A stock solution of the antibiotic at 2,000 μg/ml is prepared in a sterile suitable vehicle. Two-fold dilutions are made with sterile 1/20 Mol. phosphate buffer pH 6.5 ($KH_2PO_4$-NaOH). 1 ml quantities of each dilution are incorporated in 19 ml brain-heart infusion agar in sterile Petri dishes. The hardened surface is inoculated with test organisms and incubated 24 hours at 37° C. The minimal inhibitory concentration (MIC), i.e. the least concentration of antibiotic that completely inhibits the growth of the test organism, is expressed in μg/ml.

In some cases the MIC values were determined according to a micro serial dilution test carried out as follows: Two drops of a stock solution of the antibiotic to be tested in a known concentration are brought into the first hole of a test plate with nine numbered holes by means of a sterile Pasteur pipette. After rinsing the pipette three times with a physiological sodium chloride solution, two drops of a stock solution of the test organism in a culture medium are placed in all the holes with the exception of hole 8. In the first hole the solution of the test compound has been half diluted; then, after stirring the liquid in the first hole and adding two drops of this mixture to the second hole and so on until hole 8, dilutions of the test compound solution are obtained in geometrical progression. Hole 9 contains no antibiotic and serves for checking the growth of the test organism in a blank medium. The test plate is incubated at 30° C or 37° C for about 18 hours.

The MIC values determined according to this last test method have been placed between brackets in the following Table. The MIC values of the compounds as prepared according to the Examples 4, 5 and 7 which follow, were determined.

| | MIC values in μg./ml. Compound of Example | | | | | |
|---|---|---|---|---|---|---|
| | 5A | 7 | 4 | 5B | ampi-cillin | carbeni-cillin |
| Bacteria Gram.pos. | | | | | | |
| Streptococcus haemolyticus A 1088 | 0.4 | 9.75 | 0.75 | 1.5 | 0.75 | 0.1 |
| Streptococcus faecalis L 80 | 6 | 12.5 | 50 | 6 | 0.8 | 25 |
| Diplococcus pneumoniae L 54 | 0.75 | (12) | 25 | 6 | 0.05 | 0.75 |

-continued

|  | MIC values in μg./ml. Compound of Example | | | | ampi-cillin | carbeni-cillin |
|---|---|---|---|---|---|---|
|  | 5A | 7 | 4 | 5B |  |  |
| *Sarcina lutea* ATCC 9341 | 0.5 | (0.25) | 1.5 | (0.06) |  |  |
| Gram. neg. |  |  |  |  |  |  |
| *Haemophilus suis* A 2096 | 0.45 (1.2) | (0.9) | (0.3) | (1.2) | 0.15 | 0.8 (0.2) |
| *Brucella suis* A 2126 | 0.4 | (0.9) | 1.5 | (1.2) | 0.15 | 3 |
| *Pasteurella multocida* A 723 | 0.8 | 12.5 | 1.5 | 3 | 0.4 | 0.2 |
| *Klebsiella pneumoniae* A 809 | 100 | >100 | 100 | 100 | 25 | >100 |
| *Salmonella dublin* P 43 | 3 | 6 | 1.5 | 6 |  |  |
| *Salmonella typhimurium* R 172 | 3 | 25 | 25 | 6 | 3 | 6 |
| *Escherichia coli* U 20 | 3 | 25 | 6 | 12.5 |  |  |
| *Pseudomonas aeruginosa* H 10 | 50 | 50 | 50 | 25 | >100 | 50 |
| 2396 | 3 | 12.5 | 6 | 12.5 | 50 | 50 |
| A 1058 | 3(6) | 3(3.7) | 3(15) | 3(4) | 50 | 37 |
| *Proteus rettgeri* A 821 | 0.06 | 0.5 | 0.25 | 0.25 | 3 | 0.3 |
| *Proteus mirabilis* H 3 | 0.5 | 1.5 | 0.5 | 1.5 | 3 | 0.8 |
| L 93 | 0.12 | 1.5 | 0.5 | 0.5 | 3 | 0.5 |
| A 1200 | 0.75 (0.3) | 3(1.2) | 1.5(045) | 0.75(045) | 3 | 0.4 |
| *Proteus morganii* 2241 | 50 | 50 | >100 | 50 |  |  |

( )micro serial dilution test.

Some typical members belonging to the class of compounds of the present invention showed in initial in vivo experiments the following results. A. Serum level and secretion in urine of tested compounds and carbenicillin in rabbits after intramuscular and oral administration of a dose of 10 mg/kg.

For a quantative determination of the contents of the tested compound in blood samples, the diameters of inhibitionzones around the paperdiscs, impregnated with the sample and with samples of a serial of standard solutions of the compound to be tested in serum, are measured and the unknown content is determined by

|  | Hr. | Example 7 | | Example 5B | | Example 4 | | Example 5A | | CARBENICILLIN | |
|---|---|---|---|---|---|---|---|---|---|---|---|
|  |  | i.m. | or. | i.m. | or. | i.m. | or. | i.m. | or. | i.m. | or. |
| Serumlevel | ¼ | 81.3 | <0.25 | 25.3 | 0.3 | 27.7 | <2.5 | 23.4 | <0.57 | 14.0 | <0.25 |
| in | ½ | 68.0 | <0.25 | 18.3 | 0.3 | 20.4 | <2.5 | 19.7 | 0.64 | 6.1 | <0.25 |
| γ/ml | 1 | 38.3 | <0.25 | 10.3 | 0.3 | 9.2 | <2.5 | 13.0 | 0.64 | 2.1 | <0.25 |
| after hr | 2 | 9.6 | <0.25 | 3.3 | <0.2 | <2.5 | <2.5 | 4.7 | <0.54 | <0.25 | <0.25 |
|  | 4 | 0.43 | <0.25 | — | <<0.05 | <2.5 | <2.5 | 0.6 | <0.5 | <0.25 | <0.25 |
| % of the |  |  |  |  |  |  |  |  |  |  |  |
| secreted | 6 | 333 | 3.3 | 102 | 13.4 | 63.5 | 27.0 | 45.8 | <0.62 | 76.6 | <1.4 |
| compound |  |  |  |  |  |  |  |  |  |  |  |
| in urine | 24 | 346 | 5.9 | 110 | 20.8 | 80.9 | <29.9 | <63.0 | <1.22 | 77.9 | <2.6 |

B-E.
The ABA-test to which is referred in the following tables is carried out with groups of 6 female mice Swiss SPF of about 20 g.

After intraperitoneal or oral administration of the tested compound in a dose of 100 mg/kg in physiological saline solution, blood and urine samples are taken. The contents of the administered antimicrobial compound in these samples is qualitatively determined according to the test procedure of Vincent, by measuring the diameters of inhibitionzones around paper discs of 7 mm φ, which are impregnated with the sample and placed on an agar culture medium in a Petri dish, wherein the desired microorganism is cultured.

The average values of two or three independent runs are indicated.

means of a standard line.

The protectiontests, to which is referred in the following tables is carried out with groups of 10 female mice, Swiss SPF.

The mice of each group were infected intraperitoneally with a selected microorganism. A solution of the antimicrobial compound was administered in the indicated way and five times pro day. The duration of the treatment was one day and the duration of observation of the test animals was 7 days. The $ED_{50}$- values and the potency ratio with regard to the indicated reference compounds were determined according to probit-analysis.

B.

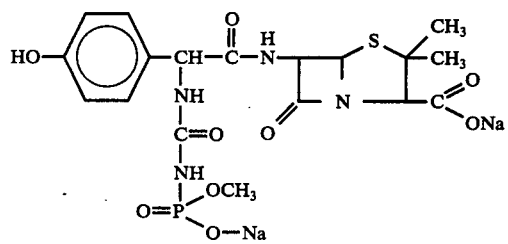

Chemotherapeutical activity

| antibacterial activity in urine (mice) Inhibition zones of urine deprived in 2½ hr in mm = ABA with regard to | Comp. Appl. 100 mg/kg | ABA | MIC γ/ml | Infection i.p. | Protection test in mice Refer. Comp. | Potency ratio administration i.p. | s.c. | oral | MIC γ/ml |
|---|---|---|---|---|---|---|---|---|---|
| Staphylococcus aur. | i.p. or. | | | Staphyl. aur A 321 | | | | | 3 |
| Staphylococcus aur. A 2001 | i.p. or. | 32 26 | 12.5 (15) | Staphyl. aur. A 2001 | | | | | |
| Staphylococcus aur. A 355 | i.p. or. | 12 7 | 100 (60) | Staphyl. aur. A 355 | | | | | |
| Escherichia coli U 20 | i.p. or. | 22 10 | 12.5 | Escher. coli | | | | | |
| Klebsiella pneum. A 809 | i.p. or. | 7 7 | 100 | Klebs. pneum. | | | | | |
| Salmon. typhimur. R 172 | i.p. or. | 25 16 | 6 | S. typhimur. R 172 | | | | | |
| Proteus mirabil. A 1200 | i.p. or. | | | Proteus mirab. A 1200 | Carb. | | 5.4 | | 0.75 (0.45) |
| Proteus mirabil. H 3 | i.p. or. | 28 14 | 1.5 | Proteus mirab. | | | | | |
| Proteus mirabil. L 93 | i.p. or. | 32 17 | 0.5 | Proteus mirab. | | | | | |
| Proteus rettgeri A 821 | i.p. or. | 26 16 | 0.25 | Proteus rettg. A 821 | Carb. Ampi. | | 4.8 0.91 | | |
| Proteus morganii 2241 | i.p. or. | 7 7 | 50 | Proteus morgan 2241 | | | | | |
| Pseudomonas aerug. A 1058 | i.p. or. | 19 7 | 3 (4) | Pseud. aerug. A 1058 | Carb. | 0.93 | 1.67 | | |
| Sarcina lutea AIC 9341 | i.p. or. | 52 47 | | | | | | | |

| blood level in mice | | | determination of blood level and urine level in rabbits (dose 10 mg/kg) | | |
|---|---|---|---|---|---|
| Test organism *Sarc. lut.* ATCC 9341) dose 100 mg/kg | appl. | | | administration way n.m. | oral |
| max. bloodlevel γ/ml | i.p. or. | 23 1.6 | Max. serum level δ/ml (i.m. = ½hr./oral = ½hr.) | 25.3 | 0.3 |
| Max. inhibition zone in mm | i.p. or. | 27 14 | % of the administered dose secreted after 24 hr | 110 | 20.8 |
| detectable inhibition zones | i.p. or. | 1½ hr ½ hr | | | |

C.

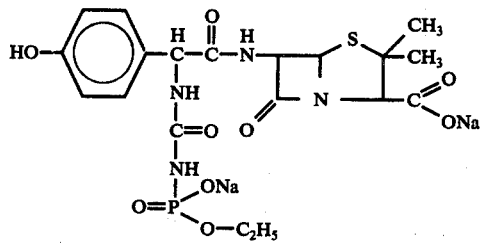

Chemotherapeutical activity

| Antibacterial activity in urine (mice Inhibition zones of urine deprived with in 2½ hr. (in mm = ABA) | Comp. Appl. 100 mg/kg | ABA | MIC γ/ml | Infection i.p. | Protection test in mice Refer. Comp. | Potency ratio administration i.p. | s.c. | oral | MIC γ/ml/ |
|---|---|---|---|---|---|---|---|---|---|
| Staphylococcus aur. | i.p. or. | | | Staphyl. aur A 321 | | | | | |
| Staphylococcus aur. A 2001 | i.p. or. | 22 13 | 25 (11) | Staphyl. aur. A 2001 | | | | | |
| Staphylococcus aur. A 355 | i.p. or. | 11 7 | 100 (30) | Staphyl. aur. A 355 | | | | | |
| Escherichia coli U 20 | i.p. or. | 24 10 | 3 | Escher. coli | | | | | |
| Klebsiella pneum. A 809 | i.p. or. | 7 7 | >100 | Klebs. pneum. | | | | | |
| Salmon. typhimur. R 172 | i.p. or. | 26 11 | 6 | S. typhimur. R 172 | | | | | |
| Proteus mirabil. A 1200 | i.p. or. | | | Proteus mirab. A 1200 | Carb. Amox. | | 2.62 | 0.16 | 0.75 (0.3) |
| Proteus mirabil. H 3 | i.p. or. | 26 13 | 0.5 | Proteus mirab. | | | | | |
| Proteus mirabil. L 93 | i.p. or. | 31 16 | 0.12 | Proteus mirab. | | | | | |
| Proteus rettgeri A 821 | i.p. or. | 31 18 | 0.06 A 821 | Proteus rettg. | | | | | |
| Proteus morganii 2241 | i.p. or. | 7 7 | 50 | Proteus morgan 2241 | | | | | |
| Pseudomonas aerug. A 1058 | i.p. or. | 19 8 | 3 (6) | pseud. aerug. A 1058 | Carb. | 2.7 | 2.5 | | |
| Sarcina lutea ATCC 9341 | i.p. or. | 51 41 | 0.5 | | | | | | |

Determination of blood and urinelevel in

-continued

| Bloodlevel in mice (Testorganism dose 100 mg/kg) | | | rabbits (Dose 10 mg/kg) | administrationway | |
|---|---|---|---|---|---|
| | appl. | | | i.m. | oral |
| max. bloodlevel γ/ml | i.p. | 37 | max. serumlevel γ/ml | 23.4 | 0.64 |
| | or. | 2 | (i.m. = ½ hr./oral = κ hr | | |
| max. inhibitionzone in mm | i.p. | 23 | % of the administered dose secreted after 24 hr. | 46–63 | <1.22 |
| | or. | 9 | | | |
| detectable inhibitionzones | i.p. | ½ hr. | | | |
| | or. | ½ hr. | | | |

D.

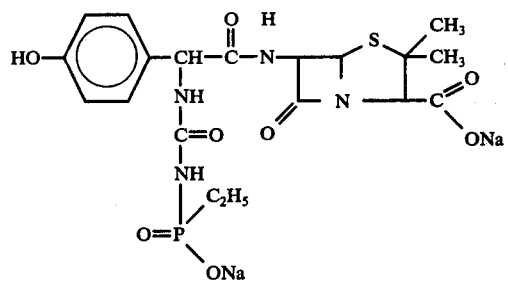

Chemotherapeutical activity

| Antibacterial activity in urine in mice (inhibition) zone of urine deprived in 2½ hr. in mm = ABA) with regard to | Comp. Appl. 100 mg/kg | ABA | MIC γ/ml | Protection test in mice | | Potency ratio | | |
|---|---|---|---|---|---|---|---|---|
| | | | | Infection i.p. | Refer. Comp. | administration | | MIC γ/ml |
| | | | | | | i.p. s.c. | oral | |
| Staphylococcus aur. | i.p. | | | Staphyl. aur. | | | | 6 |
| | or. | | | A 321 | | | | |
| Staphylococcus aur. A 2001 | i.p. | 13 | 50 | Staphyl. aur. A 2001 | | | | |
| | or. | 8 | (23) | | | | | |
| Staphylococcus aur. A 355 | i.p. | 12 | 50 | Staphyl. aur. A 355 | | | | |
| | or. | 7 | (30) | | | | | |
| Escherichia coli U 20 | i.p. | 23 | 6 | Escher. coli | | | | |
| | or. | 10 | | | | | | |
| Klebsiella pneum. A 809 | i.p. | 9 | 100 | Klebs. pneum. | | | | |
| | or. | 7 | | | | | | |
| Salmon. typhimur. R 172 | i.p. | 26 | .25 | S. typhimur. R 172 | | | | |
| | or. | 12 | | | | | | |
| Proteus mirabil. A 1200 | i.p. | | | Proteus mirab. A 1200 | Carb. | 1.23 | 1.5 (0.45) | |
| | or. | | | | | | | |
| Proteus mirabil. H 3 | i.p. | 30 | 0.5 | Proteus mirab. | | | | |
| | or. | 13 | | | | | | |
| Proteus mirabil. L 93 | i.p. | 33 | 0.5 | Proteus mirab. | | | | |
| | or. | 16 | | | | | | |
| Proteus rettgeri A 821 | i.p. | 26 | 0.25 | Proteus rettg. A 821 | | | | |
| | or. | 14 | | | | | | |
| Proteus morganii 2241 | i.p. | 7 | >100 | Proteus morgan. 2241 | | | | |
| | or. | 7 | | | | | | |
| Pseudomonas aerug. A 1058 | i.p. | 19 | 3 | pseud. aerug. A 1058 | Carb. | | | |
| | or. | 7 | (15) | | | | | |
| Sarcina lutea ATCC 9341 | i.p. | 53 | | | | | | |
| | or. | 44 | | | | | | |

| Blood level in mice Testorganism Sarc. lut. ATCC 9341) dose 100 mg/kg | | | Determination of bloodlevel and urinelevel in rabbits (dose 10 mg/kg) | administrationway | |
|---|---|---|---|---|---|
| | appl. | | | i.m. | oral |
| max. bloodlevel γ/ml | i.p. | 19 | | | |
| | or. | 4 | | | |
| max.Inhibitionzone in mm | i.p. | 22 | Max.serumlevel γ/ml | 27.7 | <2.5 |
| | or. | 12 | (i.m. = ½ hr./oral = ½ hr.) | | |
| Detectable inhibionzones | i.p. | 1½ hr | % of the administered dose secreted after 24 hr. | 80.9 | >27–<30 |
| | or. | ½ hr | | | |

E.

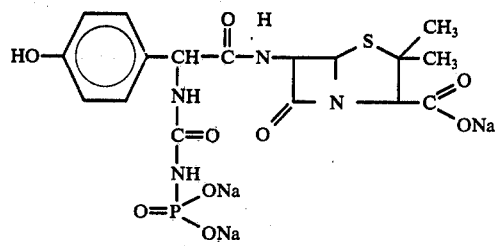

Chemotherapeutical activity

| Antibacterial activity in urine in mice (Inhibition-zones of urine deprived in 2½ hr. in mm = ABA) with regard to | Comp. Appl. 100 mg/kg | ABA | MIC γ/ml | Infection i.p. | protection test in mice | | | | |
|---|---|---|---|---|---|---|---|---|---|
| | | | | | Refer. Comp. | Potency ratio administration | | | MIC α/ml |
| | | | | | | i.p. | s.o. | oral | |
| Staphylococcus aur. | i.p. or. | | | Staphyl. aur. A 321 | | | | | 6 |
| Staphylococcus aur. A 2001 | i.p. or. | | 50 (15) | Staphyl. aur. A 2001 | | | | | |
| Staphylococcus aur. A 355 | i.p. or. | 15 7 | 100 (60) | Staphyl. aur. A 355 | | | | | |
| Escherichia coli U 20 | i.p. or. | 28 7 | 25 | Escher. coli | | | | | |
| Klebsiella pneum. A 809 | i.p. or. | 7 7 | >100 | Klebs. pneum. | | | | | |
| Salmon. typhimur. R 172 | i.p. or. | 33 16 | 25 | S. Typhimur. R 172 | | | | | |
| Proteus mirabil. A 1200 | i.p. or. | | | Proteus mirab. A 1200 | Carb. | | 10.9 | | 3 (1.2) |
| Proteus mirabil. H 3 | i.p. or. | 32 7 | 1.5 | Proteus mirab. | | | | | |
| Proteus mirabil. L 93 | i.p. or. | 36 8 | 1.5 | Proteus mirab. | | | | | |
| Proteus rettgeri A 821 | i.p. or. | 24 8 | 0.25 | Proteus rettg. A 821 | | | | | |
| Proteus morganii 2241 | i.p. or. | 7 7 | 50 | Proteus morgan 2241 | | | | | |
| Pseudomonas aerug. A 1058 | i.p. or. | 20 7 | 3 (3.7) | Pseud. aerug. A 1058 | Carb. | 1 | 1.27 | | |
| Sarcina lutea ATCC 9341 | i.p. or. | 60 34 | | | | | | | |

| Blood level in mice (Test organism Sarc. lut. ATCC 9341) | | | Determination of blood- and urine level in rabbits (dose 10 mg/kg) | | |
|---|---|---|---|---|---|
| dose 100 mg/kg | appl. | | | administration way | |
| | | | | i.m. | oral |
| Max. blood level γ/ml | i.p. or. | 134 — | max. Serum level γ/ml (i.m. = ½ hr./oral = ½ hr.) | 81.3 | <0.25 |
| Max. Inhibition zone in mm | i.p. or. | 38 7 | % of administered dose secreted after 24 hr. | 346 | 6 |
| detectable inhibition zones | i.p. or. | 2½ hr — hr | | | |

In the following examples there are several preferred embodiments to illustrate the invention. However, it should be understood that the invention is not intended to be limited to the specific embodiments.

EXAMPLE 1 sodium D-6-{α-[3-(benzyloxy(ethyl)phosphinyl-)ureido]-p-hydroxybenzylcarbonamido}penicillanate

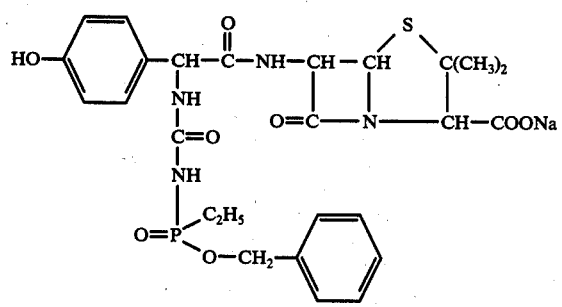

Ethyl phosphonic acid dichloride ($C_2H_5POCl_2$) with a boiling point of 78° C at 30 mm Hg was prepared in 66.6% yield from ethyl bromide and aluminium chloride phosphorus trichloride ($AlCl_3/PCl_3$) (Houben Weyl, 12$^I$, p. 397). This dichloride was converted to benzyl ethyl phosphonamidate [$C_2H_5P(O)$-$(OCH_2C_6H_5)NH_2$] in 43.7% yield by a standard method consisting of consecutive reactions with benzyl alcohol/pyridine and liquid ammonia in diethyl ether. Again employing a standard method, the isolated very hygroscopic phosphonamidate was converted with phosgene/pyridine in toluene to crude benzyl ethylphosphonisocyanatidate [$C_2H_5P(O)$ ($OCH_2C_6H_5$)-NCO]. One molar amount of the phosphonamidate was added to a mixture of one molar amount of phosgene and two and a half molar amounts of pyridine at −60° C, whereupon the temperature slowly rose to −10° C. After additional stirring for about 90 minutes at room temperature, the reaction mixture was filtered under anhydrous conditions and the filtrate was evaporated to dryness in vacuo. The amount of isocyanate in the crude product was estimated by infra-red spectroscopy.

Employing anhydrous conditions, 6.5 ml (about 26 mmol) of N,O-bis-trimethylsilyl-acetamide (BSA) were rapidly added at room temperature to a suspension of 4.75 g (about 13 mmol) of pure but not dry D(−)-(6-α-amino-p-hydroxybenzyl-carbonamido) penicillanic acid ("amoxycillin"), presumably containing about 1.0 to 1.5 moles of water per mole of penicillin, in 25 ml of dichloromethane. The resulting reaction mixture, which became clear after 10 minutes, was stirred for 90 minutes at room temperature and the clear solution was cooled to below +5° C by means of an ice-bath, whereupon a solution of an approximately equimolar amount of the above-mentioned isocyanate (prepared in crude form from 30 mmol of benzyl ethyl phosphonamidate) in 30 ml of dichloromethane was added dropwise at 0° C to 5° C. During additional stirring at about 5° C, progress of the conversion of amoxycillin was followed by thin-layer chromatography (silica; 5:4:1 mixture of ethyl acetate, acetone and acetic acid; double spot at Rf of approximately 0.7). After about 30 minutes additional stirring, a moderate conversion to the desired penicillin had taken place.

As the result was not improved after 60 minutes stirring, the reaction mixture was submitted to the usual isolation procedures. After addition of a small volume of ethyl acetate, the reaction mixture was concentrated in vacuo to a small volume and subsequently was poured into a mixture of an equal volume of diethyl ether and ice-water at a pH 7.0. The layers were separated, the organic layer discarded and the aqueous layer was washed a few times with a 1:1 mixture of ethyl acetate and diethyl ether. The remaining solution in water was acidified to pH 3.8 and was extracted 10 times with an equal volume of ethyl acetate. These extracts were combined, washed 4 times with 20 ml of ice-water saturated with sodium chloride, dried over anhydrous magnesium sulfate, filtered and concentrated slightly in vacuo to a volume of about 500 ml. A small amount of precipitate was removed by filtration and a solution of sodium α-ethyl-hexanoate in ethyl acetate was added. The formed precipitate was recovered by filtration, was washed with dry ethyl acetate and diethyl ether and dried in vacuo to obtain (about 40% based on the amoxycillin; about 18% based on the phosphonamide) of sodium D-6-{α-[3-(benzyloxy(ethyl) phosphinyl)ureido]-p-hydroxybenzylcarbonamido}•penicillanate.

According to thin-layer chromatography, IR and PMR spectra, the purity of the final product exceeded 90%.

The asymmetrically substituted phosphorus-containing group in the product constitutes a chiral centre and consequently the compound can exist in two forms. With this particular penicillin, this phenomenon is reflected on thin-layer chromatograms (two adjoining spots) and in PMR spectra. IR (KBr-disc, values in cm⁻¹): ± 3100–3500 (broad and intensive), shoulders at about 3080, 3000, 2930 and 2900, 1765, about 1690 (sh), 1665, 1600–1620, 1520, 1460, ± 1400, 1325, about 1260-1180, ± 1020, 915, 850, 745. PMR (d₆-dimethylsulfoxide (DMSO), 60 Mc, 2,2-dimethylsilapentane-5-sulfonate (DSS) as reference, δ-values in ppm): a very complicated 11H absorption area from about 0.7 to 2.2 including singlets at 1.45 and 1.57; 3.98 (s, 1H), 4.95 (centre of two doublets, δν≈0.7, J≈7.6 cps, 2H), about 5.3 to 5.5 (multiplet, 3H), 6.65 to 7.25 (q) and about 7.3 (2 signals) together 9H; 7.7 (d, J≈7.5 cps, 0.8H), about 8.4 (broad, about 0.6H) 8.85 (d, J≈8.5 cps, 0.8H).

EXAMPLE 2 sodium D-6-{α-[3-(benzyloxy(ethoxy)phosphinyl)-ureido]-p-hydroxybenzylcarbonamido}penicillanate.

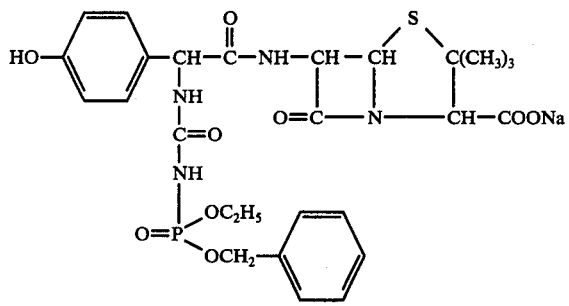

Starting from ethyl phosphorodichloridate (C₂H₅OP-(O)Cl₂), crude benzyloxy(ethoxy)phosphinylamide [(C₆H₅CH₂O) (C₂H₅O) P(O)NH₂] was prepared by a standard method consisting of consecutive conversions with benzyl alcohol/pyridine and excess liquid ammonia in diethyl ether. The crude amide (about 30 mmol) was converted according to the method in Example 1 into crude benzyl(ethyl) phosphoroisocyanatidate [(C₆H₅CH₂O) (C₂H₅O)P(O)-NCO] containing approximately 15 mmol of the isocyanate according to infra-red spectroscopy.

As described in Example 1, a suspension of 5.5 g (about 15 mmol) of amoxycillin in 25 ml of dichloromethane was reacted at room temperature with 7.5 ml (about 30 mmol) of BSA. After 60 minutes additional stirring at room temperature, the clear solution was cooled at 0° C. To this solution, a solution of the above-mentioned phosphoroisocyanatidate in 25 ml of dichloromethane was added at 0° C to +5° C over about 5 minutes. A thin-layer chromatogram taken a few minutes after completion of the addition indicated satisfactory conversion of amoxycillin to the desired penicillin (Rf about 0.65 on silica with 5:4:1 mixture of ethyl acetate, acetone and acetic acid). The reaction mixture was mixed with ice-water of pH 7.0 and a small volume of ethyl acetate. Dichloromethane was removed in vacuo and the solution in water at pH 7.0 was washed three times with a 1:1 mixture of ethyl acetate and diethyl ether. By means of the same mixture, the penicillin was removed from its solution in water at pH 3.5 to 4.0. The combined acidic extracts were repeatedly washed with small volumes of ice-water saturated with sodium chloride, dried over anhydrous magnesium sulfate, filtered and concentrated in vacuo. The final solution in ethyl acetate was treated with a solution of sodium α-ethyl-hexanoate in ethyl acetate, etc. as in Example 1 to obtain 8.0 g (about 80% based on the amoxycillin; about 40% based on the crude benzyloxy(ethoxy)phosphinylamide of sodium D-6-{α-[3-(benzyloxy(ethoxy)-phosphinyl)ureido]-p-hydroxybenzylcarbonamido}•penicillanate). Thin-layer chromatograms and PMR spectra indicated a purity of at least 95%. IR (KBr-disc, values in cm⁻¹): about 3200–3600 (broad and intensive), shoulders at about 3060 and 2935, 2980, 1768, about 1690 (sh), 1670, 1610, 1535 (sh), 1515, 1480, 1400, 1375 (sh), about 1220–1260, 1180, 1135, 1040 and 1020, 920, 840, 745, 700. PMR* (about 4:1 mixture of d₆-DMSO and DCO₂D, 60 Mc, DSS, δ-values in ppm): 1.26 (centre of two close triplets, J≈7.5 cps), 1.46 (s) and 1.58 (s)

all together 9H; about 3.85 to 4.35 (multiplet) and 4.27 (s) together 3H; 5.35 to 3.6 (AB-q, J≈4.1 cps) and 5.46 (s) together 3H; 6.7 to 7.3 (q-like, J≈8.5 cps) and about 7.4 (double signal) together 9H. * The spectrum of the compound in DMSO exhibited and usual three NH absorptions, two doublets at about 7.7 and 8.9 and a broad absorption at about 8.7.

In an analogous manner there was prepared sodium D-6-{α-[3-(benzyloxy(methoxy)phosphinyl)ureido]-p-hydroxybenzylcarbonamido}penicillanate IR (ibidem): ± 3300 -3500 (broad and intensive), ± 3050 (sh), ± 2950 (sh), 1765, about 1690 (sh), 1660, 1590-1610, 1550 (sh), 1515, 1460, 1400, 1325, about 1220-1280, 1180 (sh), 1135, 1045 (intensive) with shoulders, 930, 850, 790, 745, 700. PMR (DMSO, ibidem): 1.46 and 1.56 (6H), 3.69 (centre of two close doublets, δν≈1.3 cps, J≈11.7 cps, 3H), 3.98 (s, 1H), 5.05 (centre of two close doublets, δν≈0.5 cps, J≈7.5 cps, 2H), about 5.25 to 5.6 (multiplet, 3H), 6.65 to 7.3 (q) and about 7.35 (2 signals) together 9H, 7.8 (d, J≈8 cps, 0.8 H), about 8.4 (very broad, <1H), 8.9 (J≈8 cps, 0.8H).

EXAMPLE 3 sodium D-6-{α-[3-(dibenzyloxyphosphinyl)-ureido]-p-hydroxybenzylcarbonamido}penicillanate

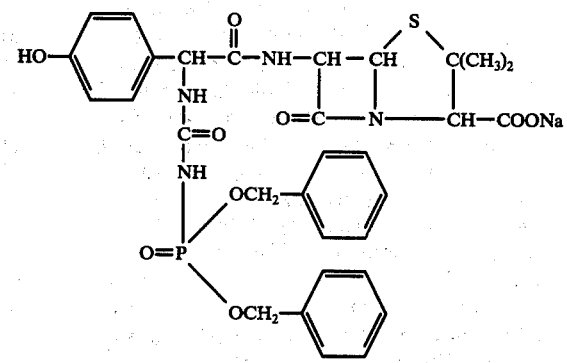

As described by O. H. Friedman et al [J. Am. Chem. Soc., 76, 916 (1954)], phosphorus trichloride (PCl$_3$) was treated in the presence of pyridine with three equivalents of benzyl alcohol in dry benzene resulting in the production and isolation of dibenzyl phosphonate [(C$_6$H$_5$CH$_2$O)$_2$P(O)H] in a 78.6% yield. This product was dissolved in dry carbon tetrachloride and gaseous ammonia was introduced (maximum reaction temperature was 38° C). Including recrystallization from carbon tetrachloride dibenzyl phosphoramidate [(C$_6$H$_5$CH$_2$O)$_2$-P(O) NH$_2$] with a melting point of 104°-105° C was obtained in 84.4% yield. This compound was converted in the usual way as described in Example 1 to crude dibenzyl phosphorisocyanatidate [(C$_6$H$_5$CH$_2$O)$_2$-P(O)NCO].

As described in Example 1, a suspension of 2.2 g (about 6 mmol) of amoxycillin in 10 ml of dichloromethane was reacted at room temperature with 3 ml (about 12 mmol) of BSA. After 60 minutes of additional stirring, the clear solution was cooled to 0° C, and then a solution of approximately 6 mmol of the above-mentioned phosphorisocyanatidate in 15 ml of dichloromethane was introduced dropwise. The reaction temperature was maintained at 0° C to +5° C. A thin-layer chromatogram taken a few minutes later indicated satisfactory conversion into the desired penicillin (Rf about 0.6 on silica with 5:4:1 mixture of ethyl acetate, acetone and acetic acid). The reaction mixture was poured into a mixture of 100 ml of ice-water and 100 ml of diethyl ether at pH 7.0. To obtain a clear two-layer system, 300 ml of ice-water and some sodium chloride were added. The layers were separated, the organic layer discarded and the aqueous layer was washed a few times with diethyl ether at pH 7.0. The remaining aqueous layer was acidified with dilute hydrochloric acid and was extracted at pH 3.5 to 4.0 with ethyl acetate. From these extracts, there was obtained as in Example 1, 3.9 g (about 90% based on amoxycillin and about 55% based on the phosphoramidate) of the virtually pure sodium D-6-{α-[3-(dibenzyloxyphosphinyl)ureido]-p-hydroxybenzylcarbonamido}penicillanate. IR (KBr-disc, values in cm$^{-1}$): about 3200-3500 (broad and intensive), shoulders at 3050 and 2980, 1780, 1680, 1620, 1560 (sh), 1520, 1465, ±1400, 1330, 1230-1270, 1190 (sh), 1140 (sh), 1030 with shoulders at 1050 and 1015, 935, 750, 710. PMR (d$_6$-DMSO, 60 Mc, DSS, δ-values in ppm): 1.45 and 1.56 (6H), 4.05 (s, 1H), 5.05 (d, J≈7.5 cps, 4H), about 5.2 to 5.6 (multiplet, 3H), 6.65 to 7.3 (q-like, J≈8 cps) and 7.35 together 14H; 7.7 (d, J≈8 cps, about 0.8H), about 8.9 (d and broad s, about 1.4H).

EXAMPLE 4 disodium salt of D-6-{α-[3-(hydroxy(ethyl)phosphinyl)ureido]-p-hydroxybenzylcarbonamido}-pencillanic acid

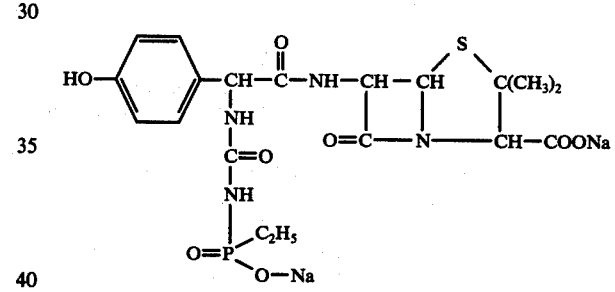

3.06 g (4.8 mmol) of sodium D-6-{α-[3-(benzyloxy(ethyl) phosphinyl)ureido]-p-hydroxybenzylcarbonamido}-penicillanate (prepared as in Example 1) was dissolved in an ice-cold mixture of 35 ml of ethanol and 5 ml of water and to the magnetically stirred solution, 1.5 g of 10% palladized charcoal were added. With continuous cooling with ice, hydrogen was passed at atmospheric pressure over the surface of the solution and during the reduction, 410 mg (4.9 mmol) of sodium bicarbonate were added in small portions. As the reduction was not completed after 4 hours, the vessel was stored overnight at 0° C and then another 1 g of the catalyst and 10 ml of ethanol were added and introduction of hydrogen was continued until completion of the reduction (a few hours). The mixture was filtered through a filter-aid using a suction pump and the filtrate was evaporated in vacuo. Absolute ethanol and benzene were added to the residue and the mixture was evaporated in vacuo. The residue was dissolved in the minimum amount of water and the volume of the solution was doubled by addition of ethanol. Acetone was added until a slight turbidity appeared and then filter-aid was added with simultaneous stirring and the mixture was filtered. Dry acetone was added to the filtrate and the resulting precipitate was recovered by filtration, washed with acetone and dried in vacuo to obtain 2.6 g (about 90%) of disodium salt of D-6-{α-[3-(hydroxy(e- thyl)phosphinyl)ureido]-p-hydroxybenzylcarbonamido}-penicillanic acid. The purity of the final product was 90% or better. On thin-layer chromatograms employing silica and a 4:1:1 mixture of n-butanol, acetic acid and water, the compound has a Rf value of about 0.1. IR (KBr-disc, values in cm$^{-1}$): 3100–3600 (broad and intensive) about 3050 (sh), 2980, 1765, 1640–1660, 1600–1615, about 1560 (sh), 1515, 1460, 1400, 1370, ± 1325, ± 1275, 1240, 1180, 1135 (sh), 1060, 900, 850, about 730. PMR (about 4:1 mixture of d$_6$-DMSO and DCO$_2$D, 60 Mc, DSS, δ-values in ppm): a very complicated 11H absorption area from about 0.7 to 2.2 including singlets at 1.46 and 1.59; 4.24 (s,1H), from about 5.3 to 5.6 (AB-q with J≈4 cps and a singlet, 3H), 6.7 to 7.3 (q-like, J≈8.0 cps, 4H).

EXAMPLE 5 disodium salt of
D-6-{α-[3-(hydroxy(ethoxy)phosphinyl)ureido]-p-hydroxybenzylcarbonamido}-penicillanic acid

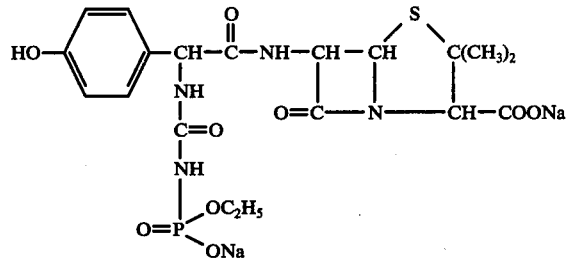

Using the procedure of Example 4, hydrogen was introduced at 0° C over the surface of a magnetically stirred mixture consisting of 3 g of 10% palladized charcoal and a solution of 6.3 g (9.7 mmol) of sodium D-6-{α-[3-(benzyloxy(ethoxy)phosphinyl)ureido]-p-hydroxybenzylcarbonamido}penicillanate (prepared as in Example 2) in a mixture of 60 ml of ethanol and 10 ml of water. During the catalytic reduction, a solution of 0.82 g (9.7 mmol) of sodium bicarbonate in 3 ml of water was introduced step-wise and the reduction was completed after 5.5 hours. The reaction mixture was filtered through a filteraid using a suction pump and the filtrate was evaporated in vacuo. To remove the remnants of water, toluene was added and the evaporation in vacuo repeated. The residue was stirred with 150 ml of pure dry acetone and the resulting colorless solid was recovered by filtration, was washed with dry acetone and dried in vacuo to obtain 5.54 g (93% yield) of pure disodium salt of D-6-{α-[3-(hydroxy(ethoxy)phosphinyl) ureido]-p-hydroxybenzylcarbonamido}penicillanic acid IR (KBr-disc, values in cm$^{-1}$): about 3200–3600 (broad and intensive), 2975, 2930 (sh), 1765, ±1650–1670, ±1610, 1550 (sh), 1515, 1460, 1400, 1375 (sh), ±1325, about 1240 (broad), 1180, 1135, 1085, 1050, 955, 900, 770. PMR (about 5:1 mixture of d$_6$-DMSO and DCO$_2$D, DSS, δ-values in ppm): 1.25 (centre of two close triplets, J≈7.5 cps), 1.46 (s) and 1.59 (s) all together 9H; about 3.75 to 4.1 (multiplet,2H), 4.22 (s, 1H); 5.42 (s) and about 5.3 to 5.6 (broadened AB-q) together 3H; 6.65 to 7.35 (q-like, J≈8.5 cps, 4H).

In an analogous manner, there was prepared the disodium salt of D-6-{α-[3-(hydroxy(methoxy)phosphinyl)-ureido]-p-hydroxybenzylcarbonamido}penicillanic acid. IR (ibidem): about 3280–3600 (broad and intensive), ±2950 (sh), 1760, 1680 (sh), about 1645 to 1665, ±1600, ±1540, 1500, 1455, 1395, 1370 (sh), 1345 (sh), 1310–1330, 1215–1245, 1180 (sh), 1125, 1080 (intensive), 1045, 895, ± 770. PMR (about b 5:1 mixture of d$_6$-DMSO and DCO$_2$D, 60 Mc, DSS, δ-values in ppm): 1.47 and 1.59 (6H), 3.50 (d, J≈11.6 cps, 3H), 4.27 (s, 1H), 5.44 (s) and about 5.35 to 5.6 (broadened AB-q) together 3H, 6.7 to 7.35 (q-like, 4H).

EXAMPLE 6 disodium salt of
D-6-{α-[3-(hydroxy(benzyloxy)phosphinyl) ureido]-p-hydroxybenzylcarbonamido}penicillanic acid

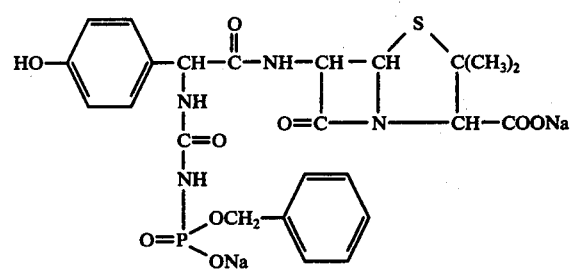

345 mg (0.47 mmol) of sodium D-6-{α-[3-(dibenzyloxyphosphinyl)ureido]-p-hydroxybenzylcarbonamido}penicillanate (prepared as in Example 3) and 80 mg (0.95 mmol) of sodium bicarbonate were dissolved in 10 ml of water. 0.1 g of 10% palladized charcoal were added, and then hydrogen was introduced at 0° C. After 5 hours of stirring, thin-layer chromatography indicated that the dibenzyl ester starting material had completely vanished from the reaction mixture while the rate of disengagement of carbon dioxide had slowed down considerably. The pH of the reaction mixture was about 8.0. The mixture was filtered through a filter-aid using a suction pump, and the filtrate was evaporated in vacuo. The residue was triturated with dry acetone and the resulting solid was collected by filtration. Ignoring the presence of inorganic salt, it estimated by thin-layer chromatograms and PMR spectra that the final product contained disodium salt of D-6-{α-[3-(hydroxy(benzyloxy)phosphinyl)ureido]-p-hydroxybenzylcarbonamido}penicillanic acid in the amount of 85–90%.

Impurities were relatively slight amounts of degradation product(s), the two-fold reduced (i.e. di-debenzylated) penicillin and acetone. As two equivalents of sodium bicarbonate were introduced, the final product should also contain somewhat less than 1 mole of sodium bicarbonate per mole of penicillin. On thin-layer chromatograms (silica, 95:5:5 mixture of methanol, acetic acid and water) the said final compound appears at Rf about 0.9 (UV positive), while the didebenzylated penicillin appears at approximately Rf 0.25. IR (KBr-disc, values in cm$^{-1}$): about 3100–3600, shoulders at ±3050, 2970 and 2935, 1765, 1690 (sh), 1640–1660, 1595–1615, ±1550 (sh), 1515, 1455, 1400, 1380 (sh), 1320–1340, 1220–1260, 1180, 1135, 1090 (intensive), 1010–1035, 985, 900, 870, 845, 750, 710. PMR (about 4:1 mixture of d$_6$-DMSO and DCO$_2$D, 60 Mc, DSS, δ-values in ppm): 1.48 and 1.60 (6H), 4.26 (s, 1H), 4.86 (d, J≈7.0 cps, 2H), 5.45 (s) and 5.35 to 5.60 (AB-q, J≈4.0 cps) together 3H); 6.65 to 7.3 (q-like, J≈8.2 cps) and about 7.35 together 9H.

The above described experiment indicates clearly that it is quite possible to obtain a mono-debenzylated reduction product in pure state because the second reduction proceeds at an appreciably slower rate. To obtain the mono-debenzylated product, it is apparent that only one equivalent of sodium bicarbonate should be employed, while further decrease in the competing formation of the product of two-fold reduction can be achieved either by employing a slightly poisoned catalyst and/or by disruption of the reduction just before complete conversion of the starting compound which is easily removed from the final product by washing with ethanol.

EXAMPLE 7 trisodium salt of D-6-{α-[3-(dihydroxyphosphinyl)ureido]-p-hydroxybenzylcarbonamido}penicillanic acid 690 mg (0.94 mmol) of sodium D-6-{α-[3-(dibenzyloxyphosphinyl)ureido]-p-hydroxybenzylcarbonamido}penicillanate (prepared as in Example 3) and 168 mg (2 mmol) of sodium bicarbonate were dissolved in 15 ml of water, 0.1 g of 10% palladized charcoal were added, and hydrogen was then introduced. After 5 hours stirring at room temperature, another 0.2 g of 10% palladized charcoal were added and the reduction was continued. After a total of 6 hours stirring, a thin-layer chromatogram indicated complete conversion of the starting material to a mixture of the product of Example 6 and the trisodium salt of D-6-{α-[3-(dihydroxyphosphinyl)ureido]-p-hydroxybenzylcarbonamido}penicillanic acid. The reduction was continued overnight and then 5 ml of water and another 0.5 g of 10% palladized charcoal were added. Reduction was then continued for 2.5 hours after which disengagement of carbon dioxide came to an end, and a thin-layer chromatogram indicated that now the compound of Example 6 had completely vanished. Acetone was added, the mixture filtered through a filter-aid and the filtrate was evaporated in vacuo. The residue was triturated with absolute ethanol and the resulting solid was recovered by filtration, was washed with ethanol and dry acetone and dried in vacuo to obtain 0.5 g (about 80% yield) of the said trisodium salt. According to thin-layer chromatograms and the PMR spectrum, the final product was about 90% pure. IR (ibidem): about 3100–3600, 2970 (sh), 1760, 1640–1660 (very intensive), 1600, 1540–1560, 1510, 1450, 1400, 1370 (sh), 1320, about 1250 with shoulders, 1180, 1135(sh), 1110 (intensive), 985 (intensive) 890, 840, 790. PMR (D$_2$O, 60 Mc, DSS, δ-values in ppm): 1.46 and 1.53 (6H), 4.20 (s, 1H), 5.2 (slightly broad s, 1H), 5.44 (s, 2H), 6.8 to 7.45 (q-like, 4H).

EXAMPLE 8 sodium D-6-{α-[3-(diphenoxyphosphinyl)ureido]-p-hydroxybenzyl-carbonamido}penicillanate

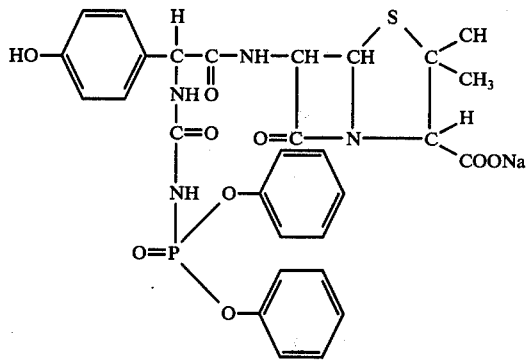

70 ml of dichloromethane were added to a suspension of 2.65 g (6.0 mmol) of α-[3-(diphenoxyphosphinyl)ureido] 4-hydroxyphenylacetic acid and of 1.4 g (7.3 mmol) of 1-ethyl-3-(3-dimethylamino-propyl)-carbodiimide hydrochloride in 25 ml of tetrahydrofuran and after stirring for 7 minutes, 1.45 g (6.6 mmol) of 6-aminopenicillanic acid which had previously been silylated with 0.97 ml (6.6 mmol) of TEA and 0.84 ml (6.6 mmol) of TMCS in 15 ml of dichloromethane, were added. After two hours, the conversion appeared to be about 40% according to thin-layer chromatography (Rf=0.7 in an acetic acid, ethyl acetate, acetone (1:5:4) mixture).

A yellow oil was formed which was separated and discarded. The resulting reaction mixture was poured into water at pH of 7 and was extracted with ethyl acetate. The pH was adjusted to 4.7 and the mixture was extracted with ethyl acetate. The extracts were dried over magnesium sulfate, were filtered and evaporated to dryness. 2 ml of sodium hexanoate were added to the residue and sodium (D-6-{α-[3-(diphenoxyphosphinyl)ureido]-p-hydroxybenzylcarbonamido}penicillanate whose alleged structure was confirmed by PMR was isolated in a yield of 1.23 g (32% yield). According to TLC, the obtained product appeared to be rather pure and probably was a D-L mixture.

EXAMPLE 9 sodium D-6-{α-[3-(benzyloxy(ethoxy)phospinyl)ureido]-p-hydroxybenzylcarbonamido}penicillanate 15 ml of dichloromethane were added to a suspension of 1.0 mmol of α-[3-(benzyloxy(ethoxy)phosphinyl)ureido]-4-hydroxyphenylacetic acid and 0.25 g (1.2 mmol) of 1-ethyl-3-(3-dimethylamino-propyl)carbodiimide hydrochloride in 4 ml of tetrahydrofuran. After stirring for about 7 minutes, 0.25 g (1.1 mmol) of 6-aminopenicillanic acid which had previously been silylated by means of 0.16 ml (1.1 mmol) of TEA and 0.14 ml (1.1 mmol) of TMCS in 2.5 ml of dichloromethane were added. After two hours, the conversion appeared to be about 50% according to thin-layer chromatography (Rf=0.7 in an acetic acid, ethyl acetate, acetone (1:5:4) mixture). The reaction mixture was poured into water at a pH of 7 and after separating an oily precipitate, the mixture was extracted with ethyl acetate. The pH was adjusted to 4.7 and the mixture was extracted with ethyl acetate. The extracts were dried over magnesium sulfate, were filtered and partial evaporation of the ethyl acetate was effected. The addition of sodium-hexanoate was made and sodium D-6-{α-[3-(benzyloxy(ethoxy)phosphinyl)ureido]-p-hydroxybenzylcarbonamido}penicillanate whose alleged structure was confirmed by PMR, was isolated in a yield of 46.6% and was according to its thin-layer chromatogram rather pure.

EXAMPLE 10

Using the procedure of Examples 1 to 9, compounds were prepared wherein $Z_1$ and $Z_2$ had the significances listed below:

| $Z_1$ | $Z_2$ |
|---|---|
| phenoxy | benzyloxy |
| methyl | benzyloxy |
| t-butyl | benzyloxy |
| i-propyl | benzyloxy |
| i-propoxy | benzyloxy |
| phenoxy | hydroxy |
| methyl | hydroxy |
| t-butyl | hydroxy |
| i-propyl | hydroxy |
| i-propoxy | hydroxy |

EXAMPLE 11

Capsules, containing as active ingredient a pencillin derivative prepared according to Example 5, were prepared in the usual way with the constituents of each capsule as listed below:

| active compound | 500 mg and | 250 mg |
|---|---|---|
| magnesium stearate | 5 – 25 mg | 2 – 15 mg |
| lactose | q.s. for 1 capsule | q.s. for 1 capsule |

The capsules may be used for oral administration.

EXAMPLE 12

Tablets, containing as active ingredient the penicillin prepared according to Example 5, were prepared in the usual way. The constituents of each tablet are listed below:

| active compound | 500 – 750 mg |
|---|---|
| polyvinylpyrrolidone | 15 – 25 mg |
| amylum maidis | 100 – 200 mg |
| magnesium stearate | 5 – 10 mg |
| lactose | q.s. for 1 tablet (about 100 – 200 mg) |

The tablets may be used for oral administration.

EXAMPLE 13

From the penicillin derivatives prepared according to Example 5, a dry powder for an injectable composition was prepared in the usual way. A quantity of 2 g and 5 g of the sterile sodium salt of the compound concerned mixed with usual ancillary substances was aseptically introduced into a vial suitable for an injectable composition under a nitrogen atmosphere. The vial was closed by means of a rubber plate, which was fixed in position by an aluminium joint ring to eliminate the exchange of gases or the penetration of microorganisms.

Usual ancillary substances may consist of glucose (usual in an amount to give rise to a final isotonic solution), buffering salts, stabilizers (e.g. $Na_2EDTA$), preservatives, wetting agents and antifoaming agents. Before use, the powder is dissolved in a suitable amount of sterile and pyrogen-free water.

EXAMPLE 14

From the penicillin derivatives of Example 5, syrups were prepared by mixing the following ingredients:

| active compound | 10 – 15 | g |
|---|---|---|
| carboxymethylcellulose sodium | 100 – 500 | mg |
| sodium saccharinate | 0.10 – 1 | g |
| methyl p-hydroxybenzoate | 0.1 | g |
| flavor | 100 – 500 | mg |
| coloring agent | 25 – 10 | mg |
| saccharose | 50 | g |
| water added to a volume of | 100 | ml |

The syrups may be used for oral administration.

Various modifications of the products and methods of the invention may be made without departing from the spirit or scope thereof and it is to be understood that the invention is to be limited only as defined in the appended claims.

We claim:
1. A compound of the formula

$$HO-\underset{}{\bigcirc}-CH-\underset{NH}{\overset{O}{\underset{\|}{C}}}-NH-CH-\underset{O=C-N}{CH}\underset{}{\overset{S}{\diagup}}\underset{}{\overset{}{\diagdown}}C\underset{CH_3}{\overset{CH_3}{\diagup}}\underset{}{\overset{}{\diagdown}}CH-COOE$$

wherein E is selected from the group consisting of hydrogen, a conventional penicillin salt forming cation, and a conventional penicillin ester forming residue which is known to improve the absorption characteristics of penicillanic compounds after oral administration to humans or animals, and Y is a group of the formula $$-\underset{O}{\overset{}{\underset{\|}{C}}}-NH-\underset{O}{\overset{}{\underset{\|}{P}}}\underset{Z_1}{\overset{Z_2}{\diagup}}$$

wherein $Z_1$ and $Z_2$ are individually selected from the group consisting of lower alkoxy, optionally substituted phenoxy, optionally substituted benzyl and benzyloxy group, optionally substituted lower alkyl, optionally substituted phenyl, hydroxy and -OM wherein M represents a conventional penicillin salt forming cation, and hydrates of the said salts.

2. A compound of claim 1 wherein the optional substituents on the groups of Y are selected from the group consisting of halogen, nitro, cyano, lower alkyl and lower alkoxy.

3. A compound of claim 1 wherein Y is selected from the group consisting of di(lower)alkoxyphosphinylaminocarbonyl, diphenoxyphosphinylaminocarbonyl, diphenylphosphinylaminocarbonyl, di(lower)alkylphosphinylaminocarbonyl, hydroxy-benzylphosphinylaminocarbonyl, hydroxy-(lower)alkoxy-phosphinyl-aminocarbonyl, hydroxy-phenylphosphinylaminocarbonyl, hydroxy(lower)alkyl-phosphinylaminocarbonyl, (lower)-alkoxy-benzyloxyphosphinylaminocarbonyl, phenyl-benzyloxyphosphinylaminocarbonyl, lower alkyl-benzyloxyphosphinylaminocarbonyl, dibenzyloxy-phosphinylaminocarbonyl, dihydroxy-phosphinylaminocarbonyl, (lower)alkoxy-benzyl-phosphinylaminocarbonyl and (lower)alkoxyphenyl-phosphinylaminocarbonyl.

4. A compound of claim 3 selected from the group consisting of D-6-{α-[3-(benzyloxy(ethyl)phosphinyl)ureido]-p-hydroxybenzylcarbonamido}penicillanic acid, D-6-{α-[3-benzyloxy(ethoxy)phosphinyl)ureido]-p-hydroxybenzylcarbonamido}penicillanic acid, D-6{α-[3-(dibenzyloxyphosphinyl)ureido]-p-hydroxybenzylcarbonamido}penicillanic acid, D-6-{α-[3-(hydroxy(ethyl)phosphinyl)ureido]-p-hydroxybenzylcarbonamido}penicillanic acid, D-6-{α-[3-(hydroxy(ethoxy)phosphinyl)ureido]-p-hydroxybenzylcarbonamido}·penicillanic acid, D-6-{α-[3-(hydroxy(benzyloxy)phosphinyl)ureido]-p-hydroxybenzylcarbonamido}penicillanic acid, D-6-{α-[3-(benzyloxy(methoxy)phosphinyl)ureido]-p-hydroxybenzylcarbonamido}penicillanic acid, D-6-{α-[3-(hydroxy(methoxy)phosphinyl)ureido]-p-hydroxybenzylcarbonamido}penicillanic acid, D-6-{α-[3-(dihydroxyphosphinyl)ureido]-p-hydroxybenzylcarbonamido}penicillanic acid, D-6-{α-[3-phenoxy(hydroxy)phosphinyl)ureido]-p-hydroxybenzylcarbonamido}penicillanic acid, D-6-{α-[3-(hydroxy(methyl)phosphinyl)ureido]-p-hydroxybenzylcarbonamido}penicillanic acid, D-6-{α-[3-(hydroxy(i-propyl)phosphinyl)ureido]-p-hydroxybenzylcarbonamido}penicillanic acid, D-6-{α-[3-(hydroxy(t-butyl)phosphinyl)ureido]-p-hydroxybenzylcarbonamido}penicillanic acid, D-6-{α-[3-(hydroxy(i-propoxy)phosphinyl)ureido]-p-hydroxybenzylcarbonamido}penicillanic acid, D-6-{α-[3-(hydroxy(t-butoxy)phosphinyl)ureido]-p-hydroxybenzylcarbonamido}penicillanic acid, D-6-{α-[3-(diphenoxyphosphinyl)ureido]-p-hydroxybenzylcarbonamido}·penicillanic acid, and their sodium, potassium, ammonium salts and mono-, di- and tri-valent amine salts, and non-toxic, pharmaceutically acceptable esters thereof.

5. A compound of claim 1 selected from the group consisting of D-6-{α-[3-(hydroxy(methoxy)phosphinyl)ureido]-p-hydroxybenzylcarbonamido}penicillanic acid and non-toxic, pharmaceutically acceptable salts and esters thereof.

6. A compound of claim 1 selected from the group consisting of D-6-{α-[3-(dihyroxyphosphinyl)ureido]-p-hydroxybenzylcarbonamido}penicillanic acid and non-toxic, pharmaceutically acceptable salts and esters thereof.

7. A compound of claim 1 selected from the group consisting of D-6-{α-[3-(hydroxy(ethoxy)phosphinyl)ureido]-p-hydroxybenzylcarbonamido}penicillanic acid and non-toxic, pharmaceutically acceptable salts and esters thereof.

8. A compound of claim 1 selected from the group consisting of D-6-{α-[3-(hydroxy(ethyl)phosphinyl)ureido]-p-hydroxybenzylcarbonamido}penicillanic acid and non-toxic, pharmaceutically acceptable salts and esters thereof.

9. An antibacterial composition comprising an effective amount of at least one compound of claim 1 and a physiologically acceptable carrier.

10. A method of combatting bacterial infections in warm-blooded animals comprising administering to warm-blooded animals a bactericidally effective amount of a compound of claim 1.

11. A disinfecting composition comprising an effective amount of at least one compound of claim 1 and a suitable inert carrier for application by washing or spraying.